United States Patent [19]
Parker et al.

[11] Patent Number: 5,755,678
[45] Date of Patent: May 26, 1998

[54] CUSTOM-FITTED BODY PROTECTIVE DEVICE WITH VARIABLE REENFORCEMENT

[76] Inventors: A. Bruce Parker, 1111 Linganore Pl., Charlotte, N.C. 28203; Ronald L. Kelley, 14625 S. Brent Dr., Huntersville, N.C. 28078; Jeffrey E. Duback, 203 Hobbs St., Davidson, N.C. 28036; Eric D. Vaughter, 5518 Cold Springs Rd., Charlotte, N.C. 28215

[21] Appl. No.: 543,162

[22] Filed: Oct. 13, 1995

[51] Int. Cl.$^6$ ............................................. A61F 5/00
[52] U.S. Cl. ......................................... 602/6; 602/8
[58] Field of Search ................. 602/5–10; 206/440, 206/441

[56] References Cited

U.S. PATENT DOCUMENTS

| | | | |
|---|---|---|---|
| 2,103,942 | 12/1937 | Gillin | 602/8 |
| 2,169,203 | 8/1939 | Hinchliff | 602/8 |
| 2,267,070 | 12/1941 | Baldwin | 602/8 |
| 2,480,849 | 9/1949 | Gersh et al. | 602/8 |
| 2,512,081 | 6/1950 | Young | 602/8 |
| 2,761,443 | 9/1956 | Parker | 602/8 |
| 2,940,884 | 6/1960 | White | 602/8 |
| 2,960,984 | 11/1960 | Parker | 602/8 |
| 3,085,569 | 4/1963 | Cook et al. | 602/8 |
| 3,557,156 | 1/1971 | Enneper | 602/8 |
| 3,631,855 | 1/1972 | Fehlau | 602/8 |
| 3,683,903 | 8/1972 | Fox et al. | 602/8 |
| 3,826,252 | 7/1974 | Laico | 602/8 |
| 3,882,857 | 5/1975 | Woodall, Jr. | 602/8 |
| 3,900,024 | 8/1975 | Lauber et al. | 602/8 |
| 3,923,049 | 12/1975 | Lauber et al. | 602/8 |

(List continued on next page.)

FOREIGN PATENT DOCUMENTS

| | | | |
|---|---|---|---|
| 0630022 | 10/1961 | Canada | 602/8 |
| 061642 | 10/1982 | European Pat. Off. | 602/8 |
| 286426 | 10/1988 | European Pat. Off. | 602/8 |
| 360020 | 12/1905 | France | 602/8 |
| 288880 | 2/1953 | France | 602/8 |
| 2004752 | 11/1969 | France | 602/8 |
| 2464076 | 9/1980 | France | 602/8 |
| 2 609 247 | of 1994 | France | 602/8 |
| 2055582 | 3/1981 | United Kingdom | 602/8 |
| 2200286 | 1/1988 | United Kingdom | 602/8 |
| 2261821 | 6/1993 | United Kingdom | 602/8 |
| 9219190 | 11/1992 | WIPO | 602/8 |

OTHER PUBLICATIONS

Cutter Biomedical, Immobilizer, pp. 1–4, Jan. 1982, Cutter Laboratories, Inc.

"Plaster Splints Aren't What They're Cracked Up to Be," Eudurasplint brochure, Carapace Inc. (1987).

Universal Plaster Splinting, Universal Plaster Splinting System, pp. 1–7, 1986, Zimmer, Inc.

Scotchcast 2 Splinting System (Undated) (Orthopedic Products Division, Minnesota Mining & Manufacturing Company).

*Primary Examiner*—Richard J. Apley
*Assistant Examiner*—Kim M. Lee
*Attorney, Agent, or Firm*—Adams Law Firm, P.A.

[57] ABSTRACT

A medical bandaging product which includes a storage package formed of moisture-impervious material and sealable to prevent entry of moisture, with a medical material positioned in the storage package and sealed therein against entry of moisture until use. The medical material includes a substrate having a variable thickness with a relatively thick predetermined central area to provide rigidity, and relatively thin predetermined edge areas to provide less rigidity to the edge areas for ease in molding the medical material around to part to be bandaged. A reactive system is impregnated into or coated onto the substrate, the system remaining stable when maintained in substantially moisture-free conditions and hardening upon exposure to sufficient moisture to form a rigid, self supporting structure. A protective wrapping encloses the substrate along its length to provide a barrier between the substrate and the skin of a patient when the material is in use.

27 Claims, 15 Drawing Sheets

U.S. PATENT DOCUMENTS

| | | | |
|---|---|---|---|
| 4,019,506 | 4/1977 | Eschmann | 602/8 |
| 4,041,941 | 8/1977 | Driver | 602/8 |
| 4,188,943 | 2/1980 | Sjöstrand | 602/8 |
| 4,235,228 | 11/1980 | Gaylord et al. | 602/8 |
| 4,279,344 | 7/1981 | Holloway, Jr. | 602/8 |
| 4,411,262 | 10/1983 | von Bonin et al. | 602/8 |
| 4,427,002 | 1/1984 | Baron et al. | 602/8 |
| 4,433,680 | 2/1984 | Yoon | 602/8 |
| 4,442,833 | 4/1984 | Dahlen et al. | 602/8 |
| 4,454,874 | 6/1984 | Monnier | 602/8 |
| 4,502,479 | 3/1985 | Garwood et al. | 602/8 |
| 4,570,622 | 2/1986 | von Bonin et al. | 602/8 |
| 4,572,171 | 2/1986 | Wegner et al. | 602/8 |
| 4,628,917 | 12/1986 | von Bonin et al. | 602/8 |
| 4,676,861 | 6/1987 | Bishop | 602/8 |
| 4,770,299 | 9/1988 | Parker | 602/8 |
| 4,869,046 | 9/1989 | Parker et al. | 602/8 |
| 4,899,738 | 2/1990 | Parker | 602/8 |
| 4,945,903 | 8/1990 | Alper | 602/8 |
| 4,989,593 | 2/1991 | Campagna | 602/8 |
| 5,003,970 | 4/1991 | Parker | 602/8 |
| 5,016,622 | 5/1991 | Norvell | 602/8 |
| 5,027,803 | 7/1991 | Scholz | 602/8 |

CUSTOM-FITTED BODY PROTECTIVE DEVICE WITH VARIABLE REENFORCEMENT

TECHNICAL FIELD AND BACKGROUND OF THE INVENTION

This invention relates to custom-fitted body protective devices such as a splint used to set broken bones and a shin, thigh, or arm pad used to protect against injuries to sports participants, and to protect previous injuries while sports competition continues. As used in this application, the terms "custom body protective device," "splint," "medical material" and "medical bandaging material" carry essentially the same meaning, and all apply to products which can be noncircumferentially-molded while flexible to a body part for curing, to thereafter form a protective structure such as a splint, as claimed.

The particular embodiments shown in the application include pre-cut and roll-form medical splinting products, and protectors of the type to be used by soccer players and other athletes during competition. The invention has application in any field—including non-sports related activities—which require or make desirable an accurate custom fit between the protective device and the body member, or which require splinting in order to immobilize the limb during healing.

The invention takes advantage of polymer chemistry to permit quick and easy molding of a medical material, such as a splint, protective pad or other protector, to the body part to be protected or immobilized. Shock attenuation is increased since the custom fit provides spreads contact between the protective device and the body member over a wider surface area.

Prior art body protectors include numerous types of guards which are fitted over the body part, such as the shin. These devices typically include a soft component to place near the skin and a hard, shell-like outer cover. The soft component is intended not only to provide a cushion, but also to accommodate itself to the varying configurations of differing sized and shaped body parts. For this reason, the cushioned part is substantially greater in thickness than required merely to provide the required amount of shock attenuation. Such devices are sufficiently "generic" that they are required to be held in place by straps or bands.

Other prior art devices include pads which are constructed of thermoplastic materials, which are heated and then formed to the body while heated. These products require a source of heat, and are susceptible to either over-or-underheating. In addition, body heat itself can soften or at least increase the flexibility of the pad, thereby decreasing the effectiveness of the protection offered by the pad. Some prior art pads include air bladders which provide an air cushion against injurious blows. Other prior art devices have a plurality of connected-together segments which are hinged for limited movement relative to each other, on the theory that such movement permits the pad to more closely conform to the body part. All of these prior art devices achieve only an approximation of a truly proper and anatomically correct fit.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

One prior art product, which was unsuccessful and is no longer marketed, included alternating layers of overlaid wide and narrow fabric strips coated with plater of paris.

In order to alleviate the above-recited disadvantages of the conventional application procedure for plaster-of-paris splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of splinting is disclosed in U.S. Pat. Nos. 4,411,262 and 4,502,479, and in applicant's prior U.S. Pat. Nos. 4,770,299, 4,869,046 and 5,003,970. The materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the splinting material.

Prior art moisture-curing systems include a package within which is contained a plurality of layers of fabric, such as fiberglass, impregnated with a moisture-curing resin. In some prior art systems, no provision is made for reclosing the package, so that the entire material must be very quickly used after removal from the package since such moisture-curing resins will cure in a relatively short period of time due merely to contact with atmospheric moisture.

From the above discussion, it can be seen that both the conventional plaster-of-paris method and the more recent moisture-curable resin splinting method possess both advantages and disadvantages. On the one hand, plaster-of-paris products are bulky, heavy and difficult to apply whereas moisture-curable resin products are lightweight, durable and relatively easy to apply. Plaster-of-paris can be very easily stored and used as needed since it has a relatively long shelf life so long as it is not completely wetted. On the other hand, the moisture-curable resins are very sensitive to the presence of even minute amounts of moisture which requires that either the materials be quickly resealed in a moisture-proof container, packaged in a wide variety of different shapes and sizes or unused portions be discarded, generating a substantial amount of waste and increasing the effective cost of the product.

In addition, multiple thickness medical materials having moisture-curable resins can sometimes be difficult to form around a limb in such a way as to completely conform the edge areas of the material to the limb. If a relatively thin structure is used, strength, impact dispersion and rigidity suffer. If a thick structure is used, strength, impact dispersion and rigidity are enhanced, but flexibility and thus ease of conformance of the material to the limb is compromised.

This invention combines the advantages of both plaster-of-paris and moisture-curable resin systems while avoiding their respective disadvantages. This is accomplished by providing a unitary medical material with improved strength and convenience. A medical material is provided with the use of moisture-curing resin materials, together with a moisture-impervious package with means for resealing the package against entry of moisture after a desired length of medical material has been removed for use. In this manner, hardening of the medical material remaining in the moisture-impervious package is prevented thereby increasing the cost effectiveness of the system substantially.

The medical material is further enhanced by providing variable reenforcement to the medical material, so that strength, impact dispersion and rigidity are enhanced, while maintaining flexibility in the edge portions.

The present invention permits quick and easy application of a protective pad to a body part in such a way as to achieve a true custom fit. The moisture curable resin system used results in a very rigid material. No heat is required, and a source of water is the only additional substance necessary to achieve a cure. Atmospheric moisture alone will cure the material into its hardened position in a relatively short period of time, but the resin in or on the material will typically be activated by dipping in water.

SUMMARY OF THE INVENTION

Therefore, it is an object of the invention to provide a medical material, such as a splint or a body protective pad, which can be molded to a body part to be protected.

It is another object of the invention to provide a medical material which has variable reenforcement for permitting greater rigidity in some areas of the pad than in others.

It is another object of the invention to provide a medical material which hardens in the presence of moisture to form a very rigid but very lightweight structure.

It is another object of the invention to provide a medical material which is stored in a moisture-proof pouch until ready for application to the body part to be protected.

It is another object of the invention to provide a medical material which is cut from a long roll of medical material stored in a moisture-proof elongate sleeve which can be rolled into a coil.

It is another object of the invention to provide a medical material which is suitable for protecting against injury, protecting injuries against further damage, and immobilizing the protected area during healing.

These and other objects of the present invention are achieved in the preferred embodiments disclosed below by providing a medical bandaging product which includes a storage package formed of moisture-impervious material and sealable to prevent entry of moisture, with a medical material positioned in the storage package and sealed therein against entry of moisture until use. The medical material includes a substrate having a variable thickness with a relatively thick predetermined central area to provide rigidity, and relatively thin predetermined edge areas to provide less rigidity to the edge areas for ease in molding the medical material around to part to be bandaged. A reactive system is impregnated into or coated onto the substrate, the system remaining stable when maintained in substantially moisture-free conditions and hardening upon exposure to sufficient moisture to form a rigid, self supporting structure. A protective wrapping encloses the substrate along its length to provide a barrier between the substrate and the skin of a patient when the material is in use.

According to one preferred embodiment of the invention, the substrate comprises a plurality of overlaid layers of fabric, some of the overlaid layers of fabric having a width greater than others of the layers to collectively define the variable thickness substrate.

According to another preferred embodiment of the invention, the fabric layers comprise fiberglass.

According to yet another preferred embodiment of the invention, at least some of the fabric layers comprise woven fiberglass.

According to yet another preferred embodiment of the invention, at least some of the plurality of fiberglass fabric layers comprise woven fiberglass and at least some of the plurality of fiberglass fabric layers comprise nonwoven fiberglass.

According to yet another preferred embodiment of the invention, the plurality of layers of fiberglass comprises at least five layers.

According to yet another preferred embodiment of the invention, the overlaid fiberglass layers are sewn together with stitches in order to provide stability to the protective pad as the medical material is formed around the body part to be protected.

According to yet another preferred embodiment of the invention, the stitches are sufficiently loosely placed in the substrate to permit substantial shifting of the individual layers relative to each other as the medical material is formed around the body part to be protected.

According to yet another preferred embodiment of the invention, the medical material is pre-cut to a length suitable for a single use and the storage package is sized to receive the single use medical material.

Preferably, the medical bandaging product is in roll form for being dispensed in user-determined lengths suitable for a given medical use, and the storage package comprises an elongate sleeve formed of moisture-impervious material and sealable to prevent entry of moisture. The medical material comprises an elongate substrate having substantially the same length as the sleeve positioned in the sleeve and sealed therein against entry of moisture until use.

Alternatively, the medical bandaging product is in roll form for being dispensed in user-determined lengths suitable for a given medical use, and the storage package comprises a pouch-like container formed of moisture-impervious material and re-sealable to prevent entry of moisture after a length has been dispensed. The medical material comprises a coiled elongate substrate sealed in the pouch-like container.

Preferably, the protective wrapping comprises a soft, flexible material covering at least one side of the substrate along its length to provide a cushioning barrier between the substrate and the skin of a patient when the material is in use.

According to yet another preferred embodiment of the invention, the protective wrapping encircles the substrate along its length.

According to yet another preferred embodiment of the invention, means are provided for resealing the sleeve against entry of moisture after a user-determined length of the bandaging product has been dispensed for use to prevent hardening of the substrate remaining in the sleeve.

In accordance with the medical material embodiment of the invention, a substrate is provided having a variable thickness with a relatively thick predetermined central area to provide rigidity, and relatively thin predetermined edge areas to provide less rigidity to the edge areas for ease in molding the medical material around to part to be bandaged. A reactive system is impregnated into or coated onto the substrate, the system remaining stable when maintained in substantially moisture-free conditions and hardening upon exposure to sufficient moisture to form a rigid, self supporting structure. A protective wrapping encloses the substrate along its length to provide a barrier between the substrate and the skin of a patient when the material is in use.

According to one preferred embodiment of the medical material, the substrate comprises a plurality of overlaid layers of fabric, some of the overlaid layers of fabric having a width greater than others of the layers to collectively define the variable thickness substrate.

According to another preferred embodiment of the medical material, the layers comprise fiberglass.

According to yet another preferred embodiment of the medical material, at least some of the fabric layers comprise woven fiberglass.

According to yet another preferred embodiment of the medical material, at least some of the plurality of fiberglass fabric layers comprise woven fiberglass and at least some of the plurality of fiberglass fabric layers comprise nonwoven fiberglass.

According to yet another preferred embodiment of the medical material, the plurality of layers of fiberglass comprises at least five layers.

According to yet another preferred embodiment of the invention, the overlaid fiberglass layers are sewn together with stitches in order to provide stability to the protective pad as the medical material is formed around the body part to be protected.

According to yet another preferred embodiment of the medical material, the stitches are sufficiently loosely placed in the substrate to permit substantial shifting of the individual layers relative to each other as the medical material is formed around the body part to be protected.

According to yet another preferred embodiment of the medical material, the medical material is pre-cut to a length suitable for a single use and the storage package is sized to receive the single use medical material.

According to yet another preferred embodiment of the medical material, the medical bandaging product is in roll form for being dispensed in user-determined lengths suitable for a given medical use, and the storage package comprises an elongate sleeve formed of moisture-impervious material and sealable to prevent entry of moisture, and wherein the medical material comprises an elongate substrate having substantially the same length as the sleeve positioned in the sleeve and sealed therein against entry of moisture until use.

According to yet another preferred embodiment of the medical material, the protective wrapping comprises a soft, flexible material covering at least one side of the substrate along its length to provide a cushioning barrier between the substrate and the skin of a patient when the material is in use.

According to yet another preferred embodiment of the medical material, the protective wrapping encircles the substrate along its length.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE MEDICAL BANDAGING PRODUCT EMBODIMENT

Figure 1:
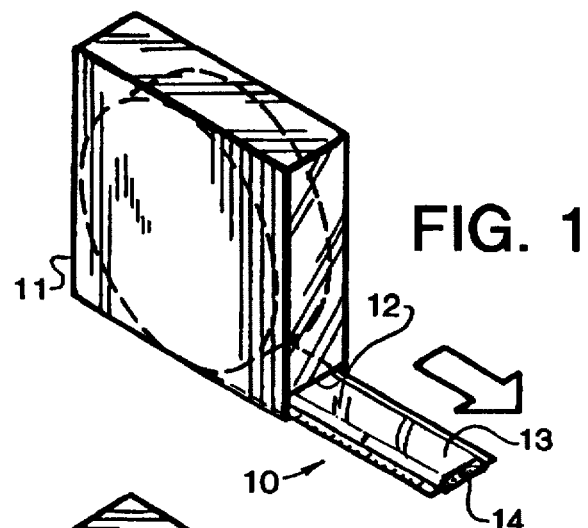
FIG. 1 is a perspective, schematic view showing the medical bandaging product being dispensed from a dispenser.

Referring now specifically to the drawings, a medical bandaging product according to the present invention is shown generally in FIG. 1 at 10. Bandaging product 10 may be sold in any convenient length, such as 15 feet, and is rolled into a coil and positioned in a suitable dispenser 11. Dispenser 11 is provided with a slot 12 at one lower corner through which bandaging product 10 extends.

Bandaging product 10 is comprised generally of an outer elongate sleeve 13 which is formed of a moisture-impervious material. Sleeve 13 is heat sealed along opposite, parallel extending sides to form an elongate tube. An elongate medical material 14, described in detail below, is positioned within sleeve 13 and is maintained in substantially moisture-free conditions until dispensed.

Figure 2:
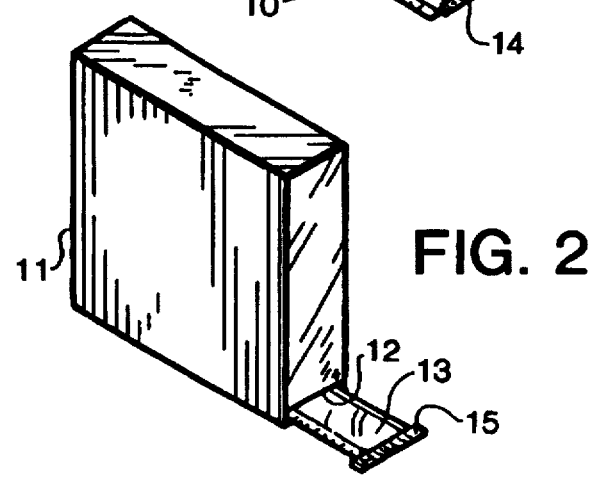
FIG. 2 is a view similar to FIG. 1, showing the unused portion of the medical bandaging product being resealed to prevent entry of moisture.

As is shown in FIG. 2, the end of sleeve 13 is sealed with sealing means, such as a moisture-impervious tape 15.

Other types of sealing mechanisms are possible such as, for example, a soft, conformable gasketing device with spring loaded compression, leverage clamping or screw action of sufficient strength to prevent entry of moisture into sleeve 13. One particularly suitable device (not shown) is a pair of spring loaded rollers which, as compression takes place rolls slightly backwards, pushing medical material 14 back slightly into sleeve 13 to permit a better seal.

Another possible sealing means (not shown) is a device which pushes the medical material 14 back into the sleeve 13 a sufficient distance (approximately one inch), so that the open end of sleeve 13 may be heat sealed once again.

Figure 3:
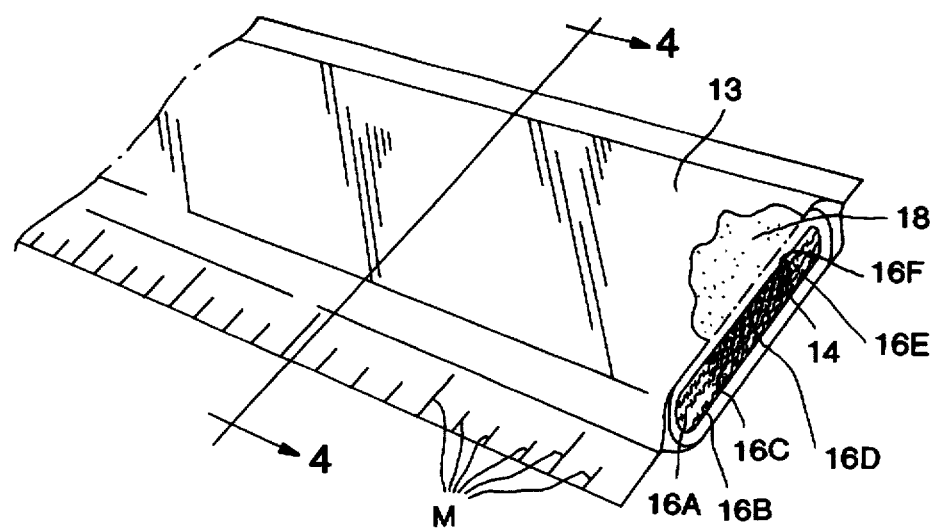
FIG. 3 is a perspective view with parts broken away of a cut length of medical material.

Since the appropriate length of medical material 14 is best determined by measurement, measurement marks "M" are printed on one edge of the sleeve 13, as is best shown in FIG. 3. Once the appropriate length of medical material 14 has been dispensed and cut from the roll, it is removed from sleeve 13 and sleeve 13 is discarded.

Figure 4:
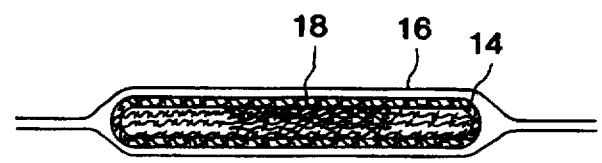
FIG. 4 is an enlarged vertical cross-section taken substantially along lines 4—4 of FIG. 3.
Figure 5:
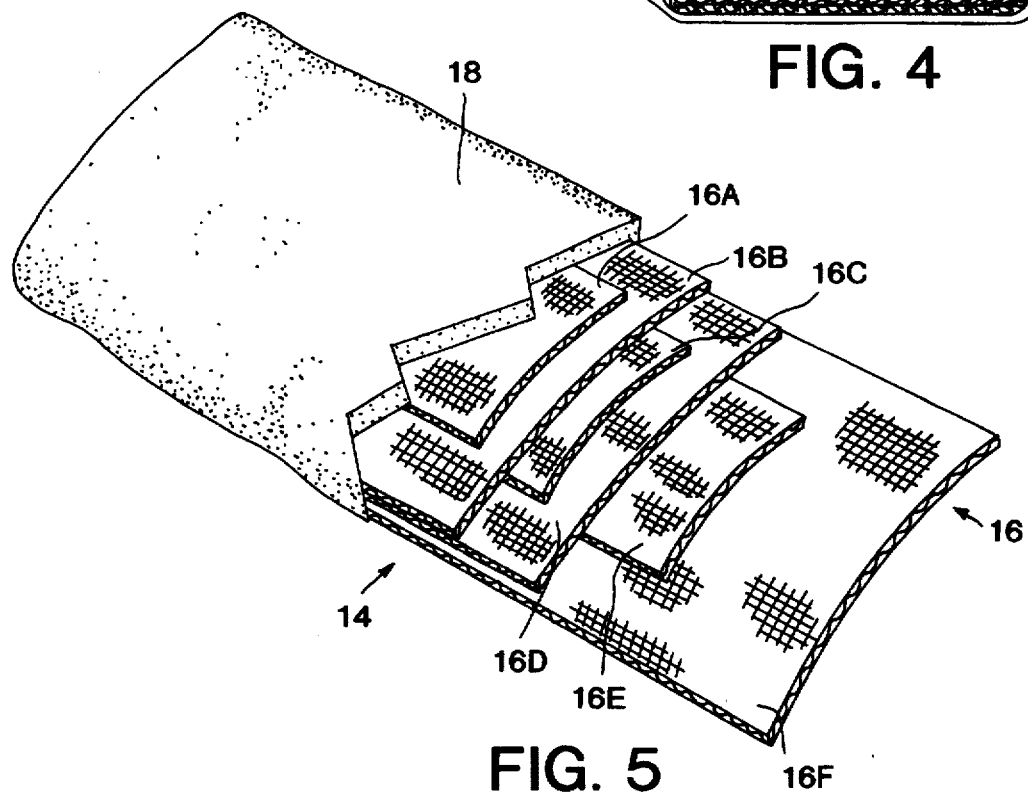
FIG. 5 is a perspective view of a length of the medical material with the substrate layer exposed for clarity.

Referring now to FIGS. 4 and 5, medical material 14 comprises a substrate 16 comprised of a suitable number for example, 6, of overlaid layers 16A–16F of a woven or knitted relatively open fabric—preferably fiberglass. Substrate 16 is contained within a tubular wrapping 18 which is formed of a soft, flexible non-woven fiber such as polypropylene or some other suitable hydrophobic fiber. This provides a cushioning protective layer between the skin of the patient and substrate 16. The layers 16A–16F of substrate 16 are impregnated or coated with a reactive system which remains stable when maintained in substantially moisture-free conditions but which hardens upon exposure to sufficient moisture to form a rigid, self-supporting structure. A typical formulation of the reaction system is set forth in the following table:

| Typical Formulation: | | |
| --- | --- | --- |
| Isonate↓ 143L or Mondur↓ CD or Rubinate ↓ XI168 | polyisocyanate | 50.0% |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262, referred to above.

Figure 6:
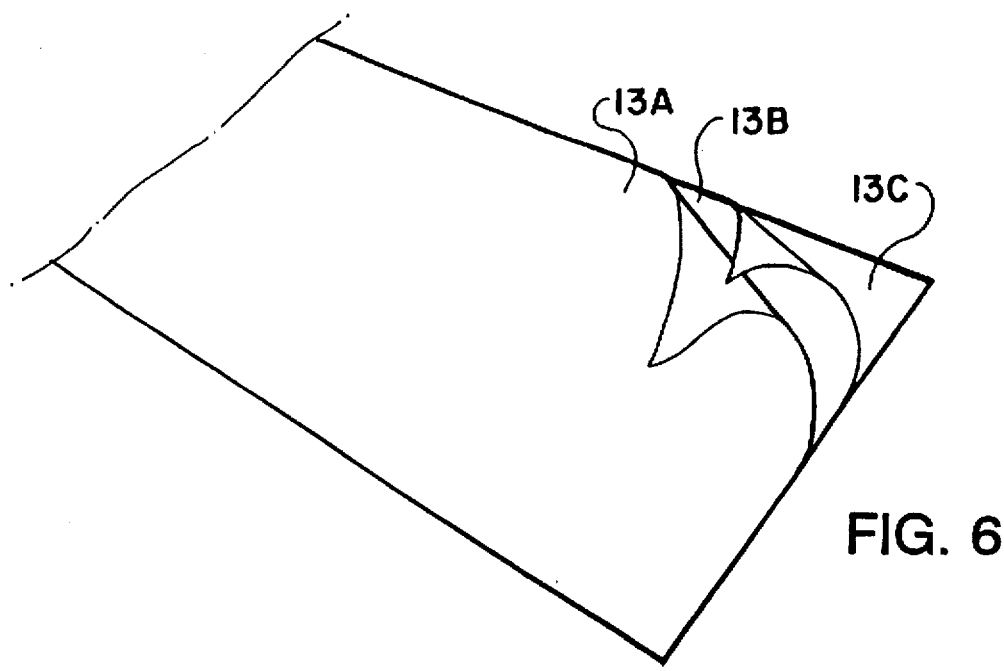
FIG. 6 is a perspective view illustrating the laminate structure of the elongate outer sleeve.

As in shown in FIG. 6, sleeve 13 is formed of two laminated elongate sheets placed in registration and heat sealed along its opposite sides to form a tube. The outer layer 13a is formed of a tear-resistant plastic film. The middle layer 13b comprises aluminum foil and acts as a moisture barrier. The inner layer 13c is a plastic film having thermoplastic properties suitable for heat sealing the interior of sleeve 13 securely against moisture.

Figure 7:
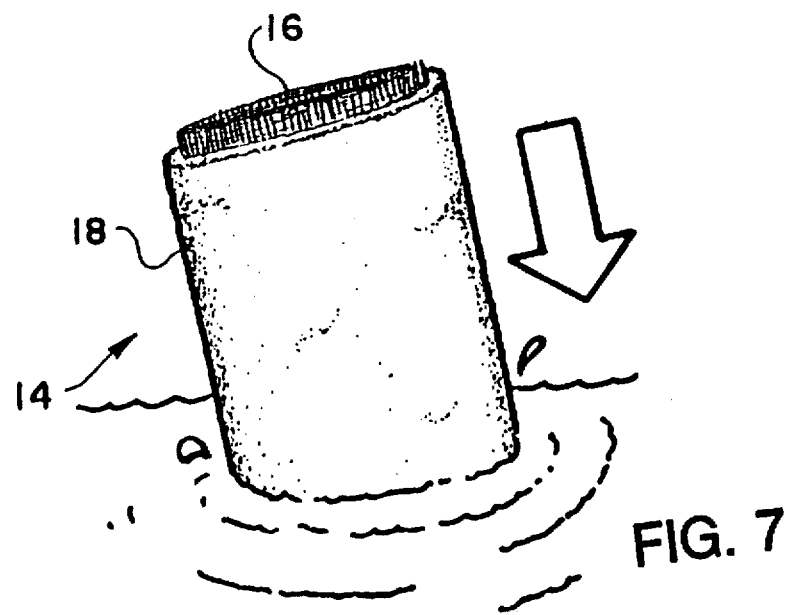
FIG. 7 illustrates activation of the moisture-curable resin of the invention by wetting.

As is shown in FIG. 7, moisture-curing is activated by dipping product 14 in water. Then excess moisture is squeezed from the structure.

Figure 8:
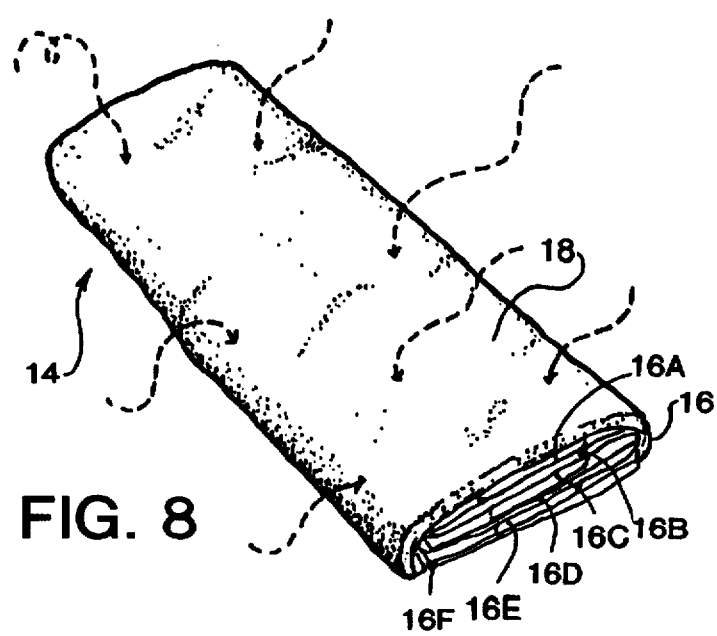
FIG. 8 illustrates activation of the reactive hardening system of the invention by contact with atmospheric moisture.

Alternatively, moisture-curing can take place over a longer period of time by allowing contact between the reactive system on substrate 16 and atmospheric moisture, as is illustrated in FIG. 8.

Referring again to FIG. 5, the fiberglass fabric layers 16A–F can be die-cut to shape, or formed by other conventional processes. As described below, the various fabric layers 16A–F have different widths, and the degree of overlap and non-overlap resulting from these differing widths has the effect of providing the a variable thickness with a relatively thick predetermined area where increased rigidity is desirable and a relatively thin area where increased flexibility is desirable. Ordinarily, the thickest area will be in the central portion of the material 14, while the edge areas of the material 14 are less thick.

Alternatively, some of the layers 16A–F may be of other material, such as polypropylene, which offers additional flexibility and some cost savings in material. Various patterns of varying widths of the layers 16A–F can be used. In addition to the pattern shown in FIG. 5, other suitable patterns are shown below in FIGS. 24A–27B, which also apply to the protective pad version of the invention.

Figure 9:
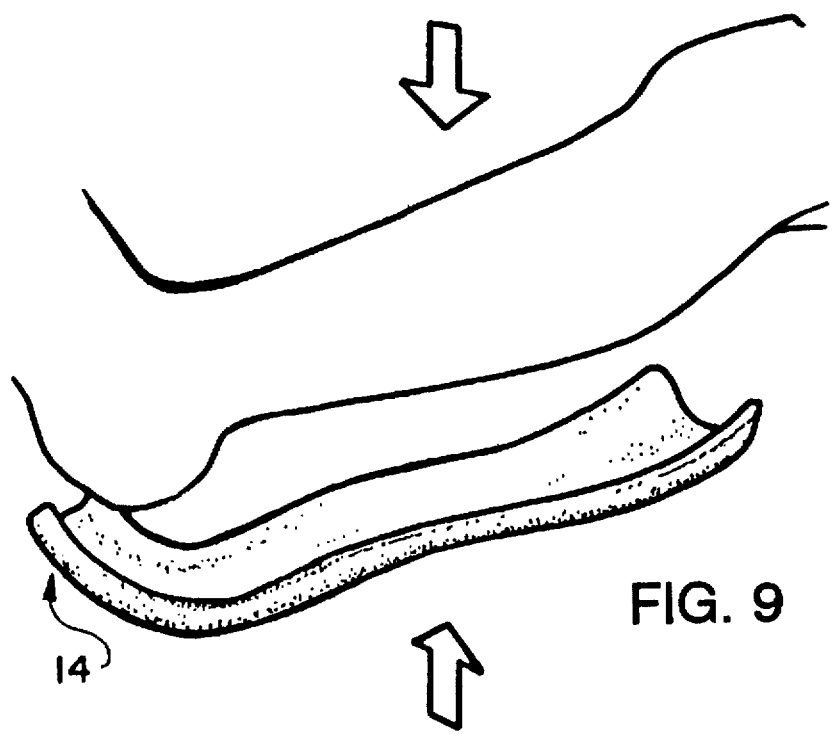
FIG. 9 shows the medical material after removal from the sleeve being formed to fit the contour of a body member.
Figure 10:
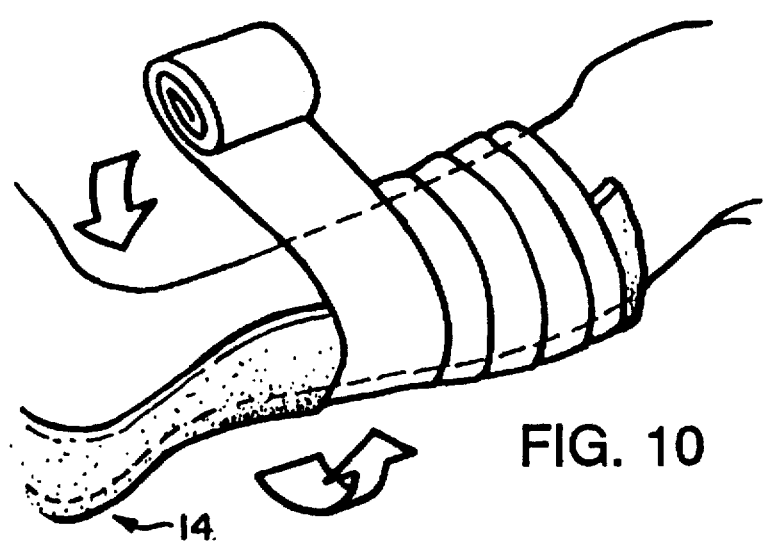
FIG. 10 is a perspective view of the hardening medical material being secured into place on a body member by means of a covering wrap.

Referring now to FIG. 9, an appropriate length of the material 14 is formed in the shape of the body member to be immobilized. This particular type of splint, known as a posterior short leg splint, is formed by molding a length of the product 14 to the calf and up over the heel and onto the foot. The differing widths of the layers 14A–F assist in wrapping the material 14 securely around the limb and closely conforming the material to the limb. This structure also permits a very lightweight but strong bandaging material 14. After the material 14 is applied to the limb, it is overwrapped with a conventional elastic bandage, as is shown in FIG. 10. The elastic bandage holds the material 14 securely and conformably to the limb until the material has completely cured into a hard splint structure which provides substantial support to the limb.

PROTECTIVE PAD EMBODIMENT

Figure 11:
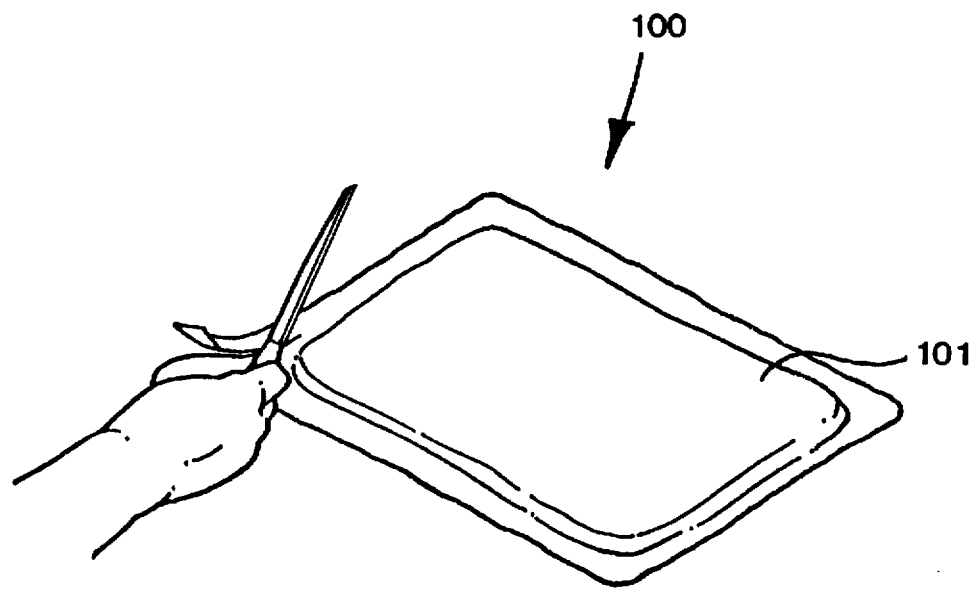
FIG. 11 is a perspective view showing the packaging within which the protective pads according to the invention may be stored until use.
Figure 12:
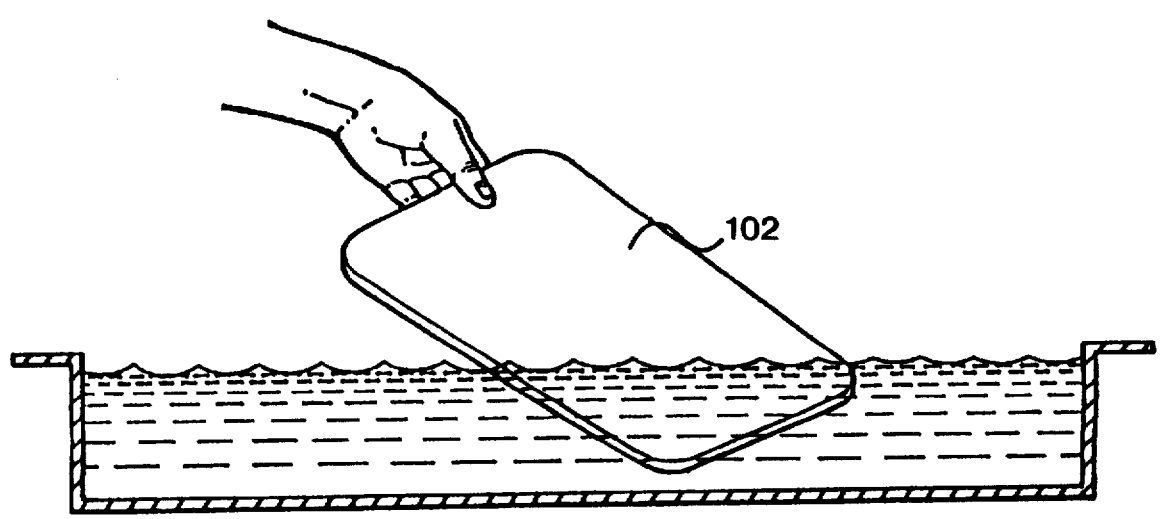
FIG. 12 illustrates that the protective pad is wetted in water before application.
Figure 13:
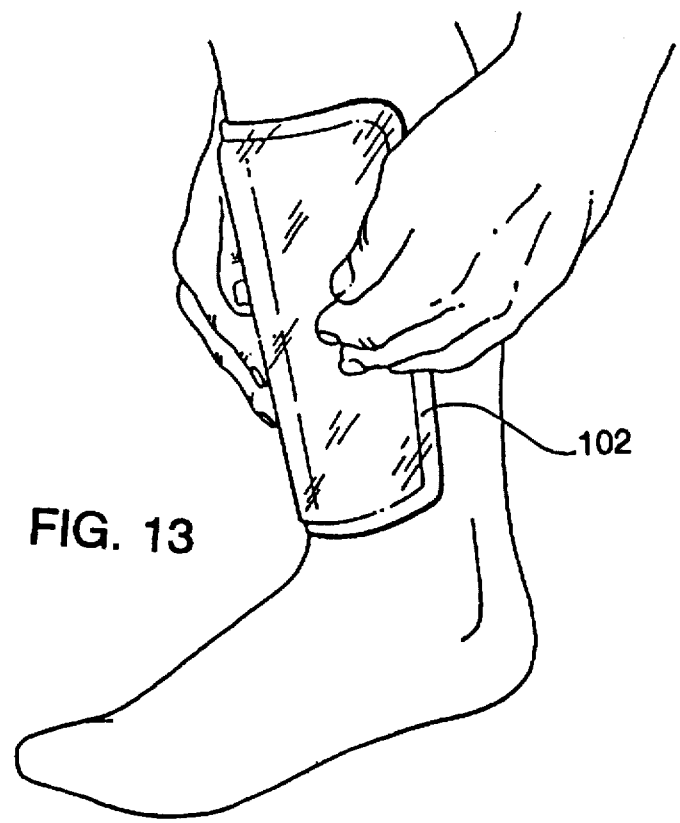
FIGS. 13, 14 and 15 are sequential perspective views of a protective pad according to one embodiment of the invention being molded to the lower part of the leg.
Figure 14:
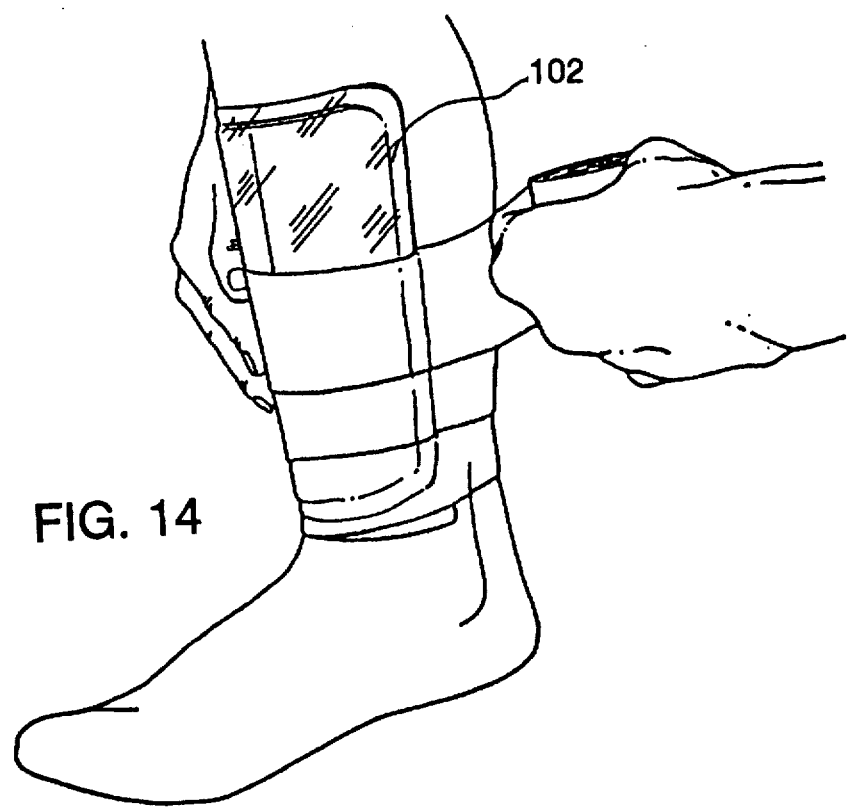

Referring now specifically to the drawings, FIGS. 11–15 illustrate a protective pad assembly according to another embodiment of the invention. In general, to create the custom body protective device according to any of the particular embodiments disclosed in this application, a protective pad assembly 100 is utilized. A moisture-impervious foil and plastic laminated pouch 101 is opened with scissors or a knife, as shown in FIG. 11, and the protective pad 102 is removed. As is shown in FIG. 12, the pad 102 is dipped in water to activate the moisture-curable resin with which the pad is impregnated or coated. The wet pad 102 is then applied to the body part to be protected. As is shown in FIG. 13, the pad 102 is applied to the shin of the leg and held there while it is overwrapped with, for example, an elastic bandage, as is shown in FIG. 14. The pad 102 will harden within a matter of minutes, and will retain the conformation in which it was held during curing.

The pad 102 can be worn directly next to the skin and under, for example, a game sock. Since the pad 102 was molded directly next to the skin, the fit is virtually perfect, and fits so well that straps or belts are not ordinarily needed. The pad 102 is held in place by the sock and the adherence of the pad 102 to the corresponding shape of the shin.

Figure 15:
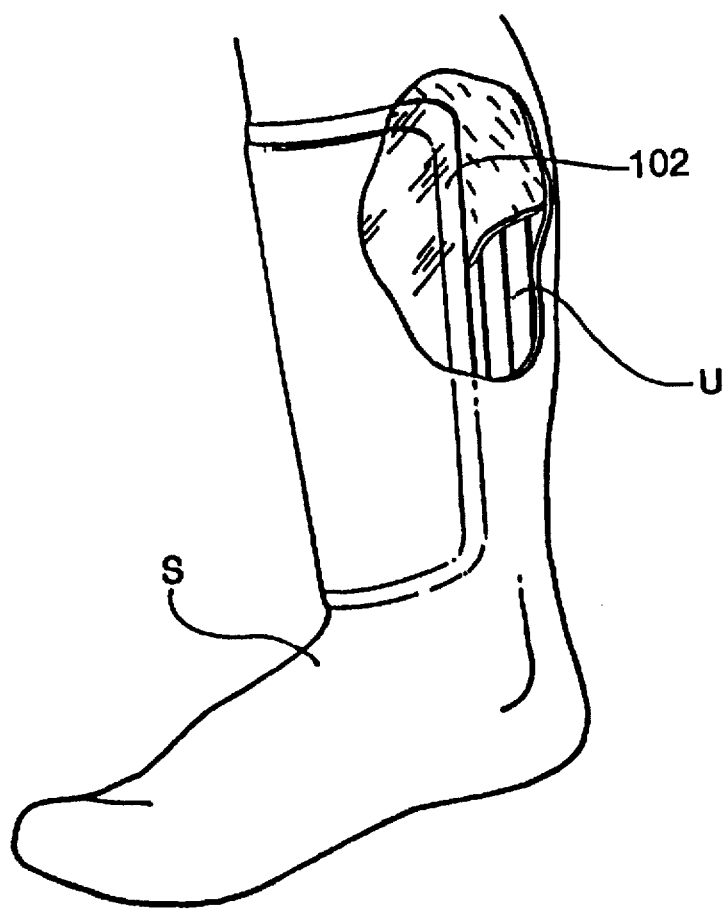

Alternatively, the pad 102 can be worn over an undersock "U" and under a game sock "S", as is shown in FIG. 15. Ordinarily, pad 102 will fit acceptably over the undersock "U" even if molded directly over the skin. However, the pad 102 can be molded onto the shin while the wearer is wearing an undersock, if the pad 102 is to be normally worn over an undersock.

Alternatively, an integral, long strip of multi-layer material in the form of an elongate pad member may be sealed after fabrication into a moisture-proof pouch. (Not shown). The pouch can be sealed against moisture intrusion between uses by a clamp.

When needed, the clamp is released and the elongate pad member is pulled through the pouch opening and cut to separate a single body protective pad from the elongate pad member. Thereafter, the pad member is used as described above with reference to FIGS. 12–15.

Figure 16:
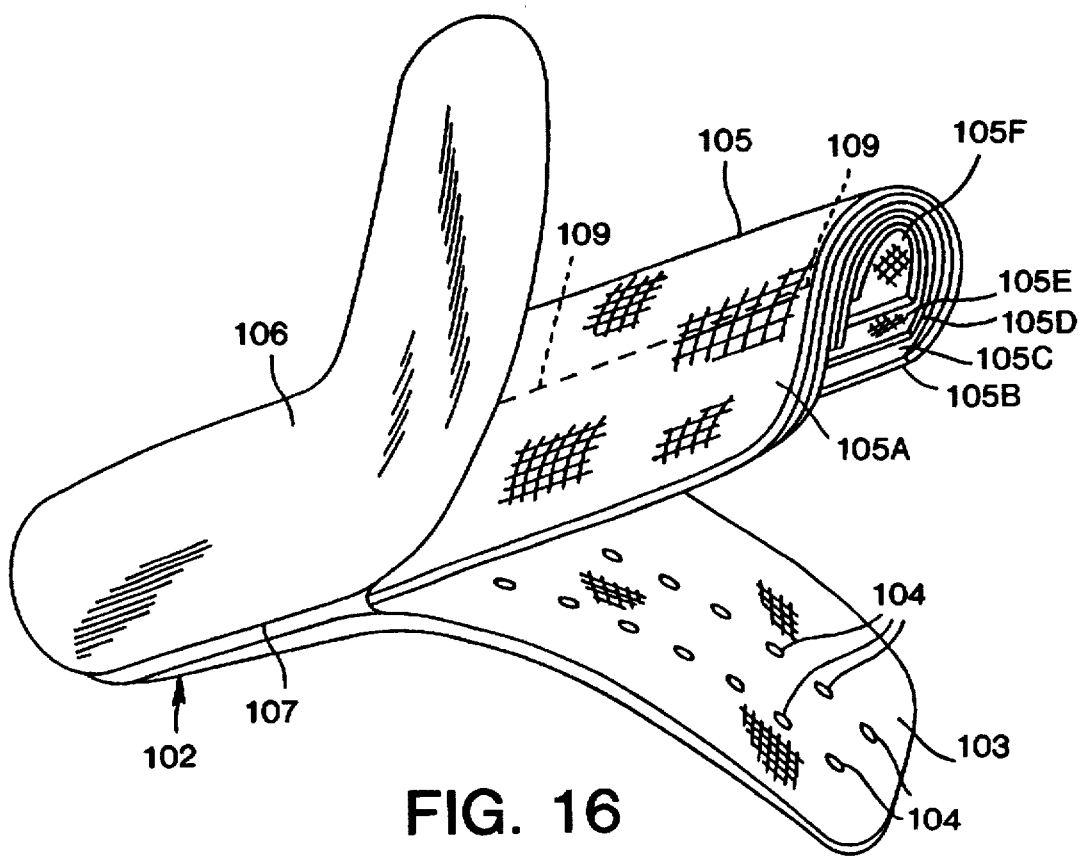
FIG. 16 is a perspective view of a partially-disassembled protective pad embodiment according to an embodiment of the invention.

Referring now to FIG. 16, the pad 102 is illustrated and described more specifically. Pad 102 is shown in its molded configuration after the steps carried out as described with reference to FIGS. 11–15. Pad 102 is a multi-layer protective pad for being custom-fitted to a body member to be protected, for example, the shin of the leg. A flexible inner cushion layer 103 is provided for being placed closest to the body member. Inner cushion layer 103 is preferably a laminated one-eighth inch, six pound EVA (ethylene vinyl acetate) with a heavy knitted covering, such as a product known as Tietex. Other thicknesses and weights of cushioning, both laminated and unlaminated, can also be used. Holes 104 are provided for ventilation. The cushioning provides a comfortable surface next to the skin or under sock. The EVA is flexible enough to bend easily with the other components of the pad 102.

An initially flexible intermediate layer 105 is bonded to the inner cushion layer 103. The intermediate layer 105 is preferably formed of fiberglass fabric impregnated with a moisture-curable resin which hardens upon curing to form a rigid structure which retains shape of the body part onto which it is molded during curing.

In accordance with the invention, the intermediate layer 105 is composed of several individual fiberglass fabric layers 105A–F, which are preferably die-cut to shape. As described below, the various fabric layers 105A–F have different widths, and the degree of overlap and non-overlap resulting from these differing widths has the effect of providing the a variable thickness with a relatively thick predetermined area where increased rigidity is desirable and a relatively thin area where increased flexibility is desirable.

Alternatively, some of the layers 105A–F may be of other material, such as polypropylene, which offers additional flexibility and some cost savings in material.

As is also shown in FIG. 16, a flexible outer layer 106 is bonded to the intermediate layer 105 and is held by the intermediate layer 105 in the same body-part defined shape as the intermediate layer 105. The outer layer 106 is preferably a polyester double-knit fabric having "all way" stretch.

The two outer components of the protective pad 102—the inner cushion layer 103 and the outer layer 106—are seamed together and placed into a closed envelope with a relatively close overedge seam 107, enclosing the intermediate fiberglass layer 105 inside without actually catching the intermediate fiberglass layer within the stitches.

Figure 17:
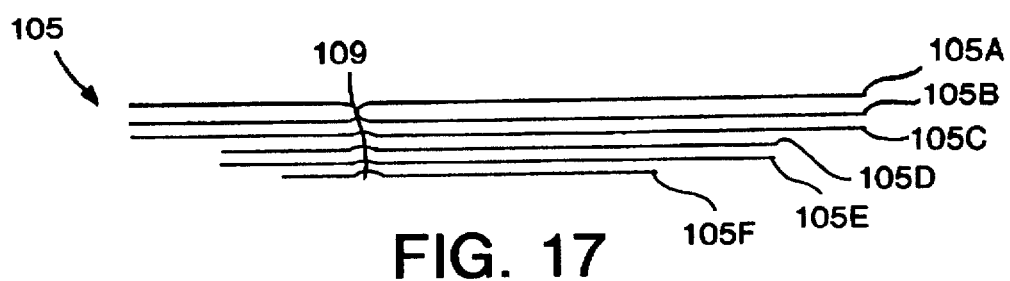
FIG. 17 is a simplified vertical cross-sectional view of the intermediate layers of fiberglass in a protective pad according to an embodiment of the invention.

Referring now to FIG. 17, the intermediate layer 105 shown in FIG. 16 is shown schematically in cross-section for purposes of further explanation. As noted above, the intermediate layer 105 is formed of six fiberglass layers 105A–F, as described above. The relative widths and dimensions of the layers 105A–F can vary. Generally, the outermost layers 105A–C are the widest—on the order of five inches from side-to-side. The layers 105A–C provide basic strength to the pad 102 from side-to-side while permitting some flexibility.

Layers 105D and 105E are narrower—on the order of four inches wide, and provide additional strength in the central part of the pad 102 while providing some residual flexing.

The single layer 105F is narrower still—three inches—and provides further reenforcement for the center of the pad 102. The thinner side edge areas permit better conformance of the pad 102 to the body member during molding. After curing is complete, the central, longitudinally-extending area of the pad 102 is quite rigid and provides substantial impact resistance, while the edges of the pad 102 retain sufficient flexibility to move minimally if pressure is directly applied. As is shown in FIG. 16, the pad 102 is applied to the leg with the narrowest fabric layer 105F nearest the leg.

Alternatively, the respective differing widths of fabric layers 105A–F can be five inches, three inches and two inches.

As also shown in FIG. 17, sewing stitches 109 bind the six layers 105A–F together into a loosely-held unit which maintains its longitudinal alignment as it is applied to the body part. Looseness is desirable since the intermediate layers 105A–F are intended to be bent into an arc. The collective thickness of the layers 105A–F results in substantial lateral shifting of the fabric layers 105A–F relative to each other. The sewing stitches 109 are applied to the fabric layers 105A–F with only slight tension and relatively widely spaced-apart. A stitch length of from six to 10 stitches per inch will provide sufficient looseness to permit the layers 105A–F to shift laterally relative to each other while maintaining overall longitudinal alignment. Tension should be sufficiently loose so that there is no tendency for the fabric layers 105A–F to be drawn inwardly towards each other by the stitches 109, but conversely, the fabric layers 105A–F maintain the spacing from each other naturally caused by the stiffness, thickness and irregularity of the fabric surfaces. The stitches are put in sufficiently loosely so that there is no tendency for the stitches to perforate the fiberglass fabric layers along the line of the stitching.

Note that the stitches 109 are applied asymmetrically, that is they extend along the length of the pad 102 closer to one side edge of the intermediate layer 105 than to the opposing side edge. This enables the fabric layers 105A–F to shift to a greater degree than if the stitches ran down the center of the intermediate layer 105.

It has been determined that this structure, generally referred to as a "pyramid structure" disperses impact across the width of the body part more efficiently than a pad with multiple layers, all having the same width.

Referring now to FIGS. 18–23, several different constructions of the invention according to the application are illustrated. Each of these constructions contain the same basic three components—the inner layer 103, intermediate layer 105 and outer layer 106—as the pad 102 already described in detail in reference to FIGS. 11–17.

Figure 18:
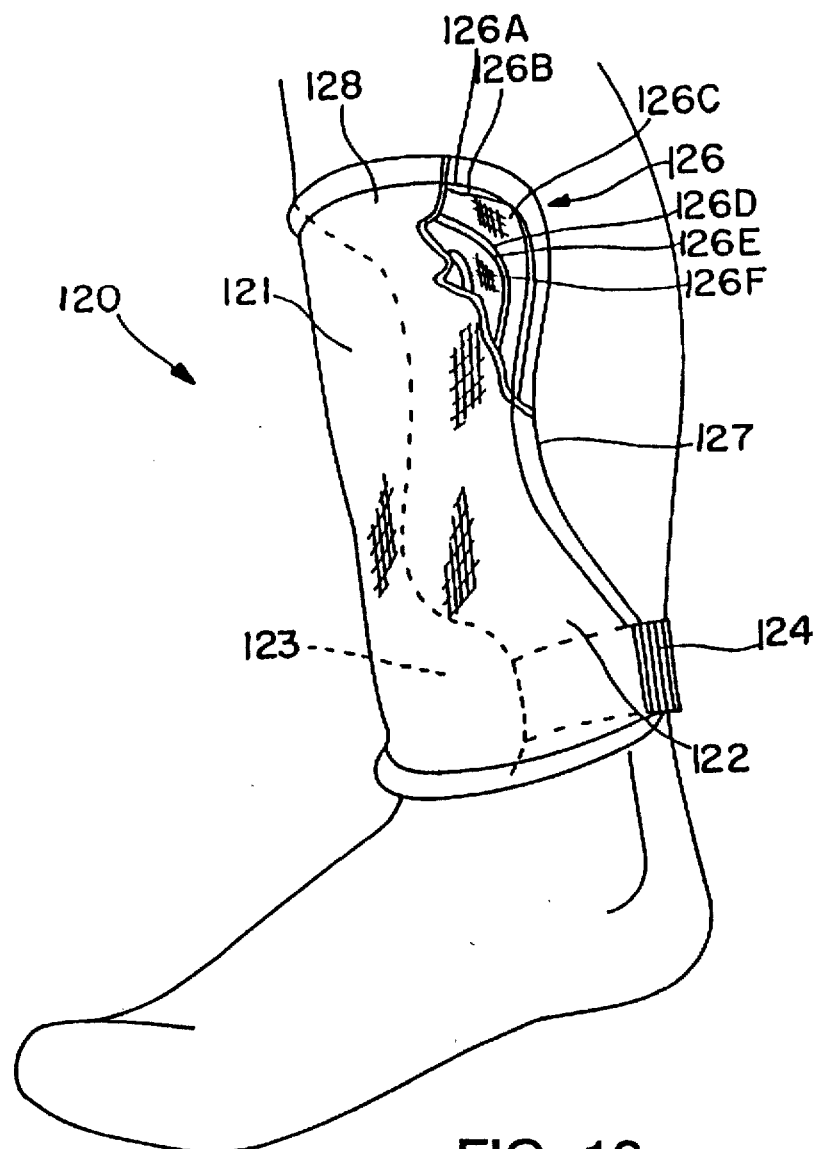
FIG. 18 is a perspective view of another embodiment of the invention.

FIG. 18 illustrates a shin guard 120 with a relatively narrow center portion 121 and two integrally-formed side portions 122 and 123 extending outwardly from the center portion 121 for protecting the opposing sides of the shin. A strap 124 may be used to retain the shin guard 120 snugly on the leg. The strap 124 may be a heavy elastic strap connected to both side portions 122 and 123 which is stretched sufficiently to allow the foot to pass through when the shin guard 120 is being placed on the foot, or a hook-and-loop system, with a small patch of hooks or loops attached to one of the end portions 122 or 123 and the strap having a length of complementary material attached for mating with the patch.

As is shown in FIG. 18, the body of the shin guard 120 has an intermediate layer 126, which is made up of three relatively wide fiberglass layers 126A, B and C, two narrower layers 126D and E, and a narrow central layer 126F. Thus, the shin guard 120 exhibits greater flexibility along the opposing sides than in the middle.

The intermediate layer is sandwiched between an inner cushion layer 127 and an outer layer 128 substantially as described above.

Figure 19:
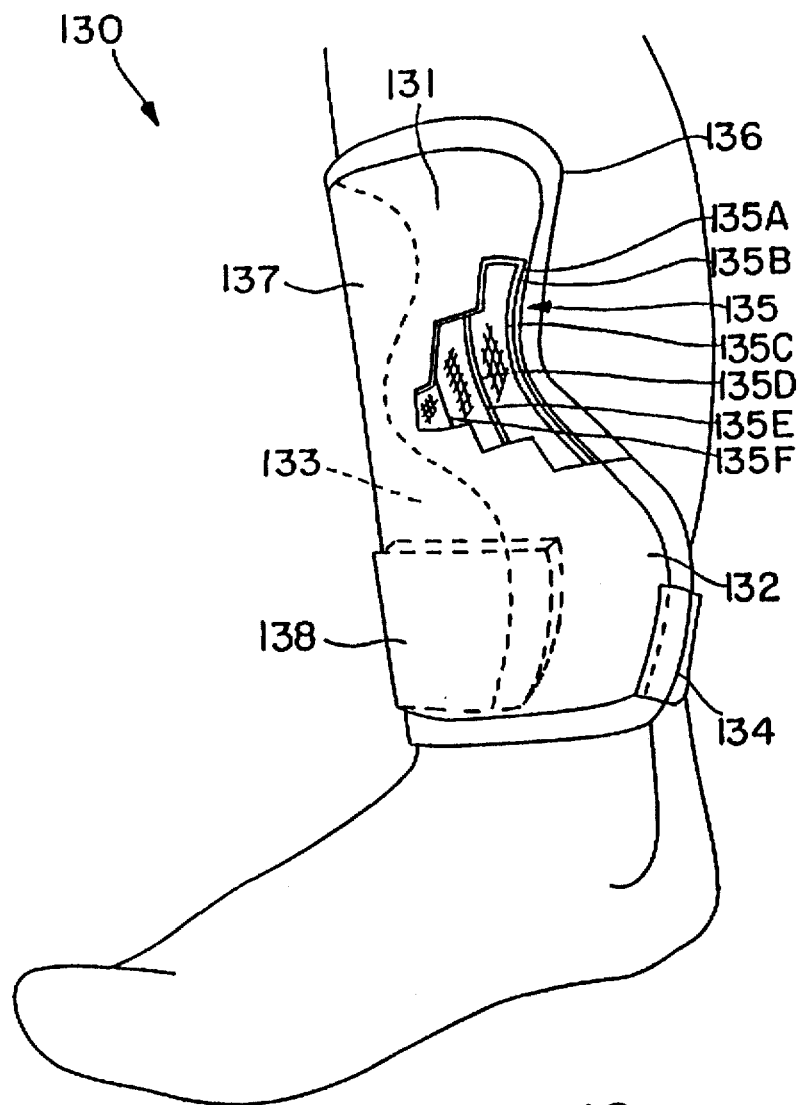
FIG. 19 is a perspective view, with parts broken away, of yet another embodiment of the invention.

FIG. 19 illustrates a shin guard 130 with a relatively narrow center portion 131 and two integrally-formed side portions 132 and 133 extending outwardly from the center portion 131 for protecting the opposing sides of the shin. A strap 134 may be used to retain the shin guard 120 snugly on the leg.

The body of the shin guard 130 has an intermediate layer 135, which is made up of three relatively wide fiberglass layers 135A, B and C, two narrower layers 135D and E, and a narrow central layer 135F. Thus, the shin guard 130 exhibits greater flexibility along the opposing sides than in the middle.

The intermediate layer 135 is sandwiched between an inner cushion layer 136 and an outer layer 137 substantially as described above.

In addition, a supplemental reenforcement pad 138 is applied to the front portion of the shin guard 130 at the area of the shin just above the top of the foot.

Figure 20:
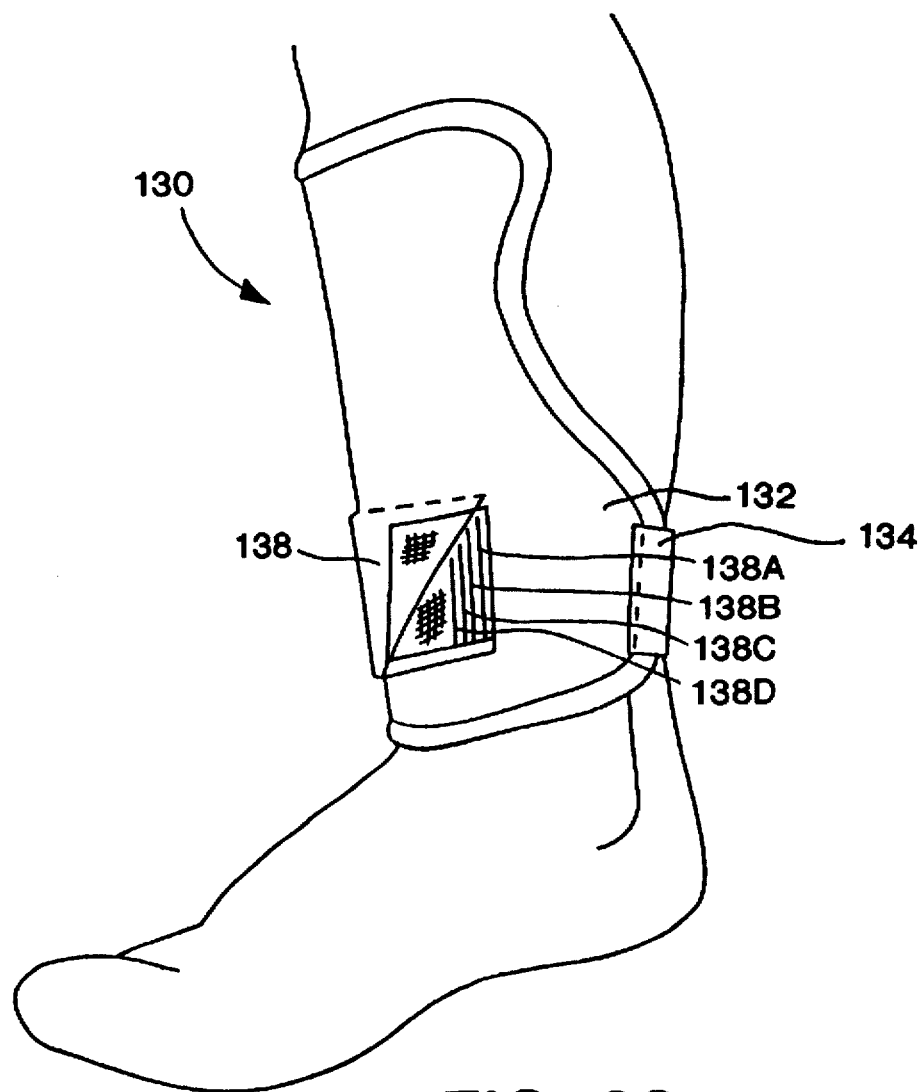
FIG. 20 is a perspective view of the embodiment of the invention shown in FIG. 19 with part of the outer layer broken away to show the additional reenforcement.

As is shown in FIG. 20, reenforcement pad 138 is formed of an additional four layers of fiberglass fabric 138A–D. Each of the layers 138A–D are the same size and overlie each other in substantial registration with each other. The fiberglass fabric of the layers 138A–D is impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure along with the other layers of fiberglass 136A–F of the intermediate layer 135. Thus, in the area of the reenforcement pad 138 there are ten overlying layers of fiberglass—six in the intermediate layer 135 and four in the impact pad 138.

Figure 21:
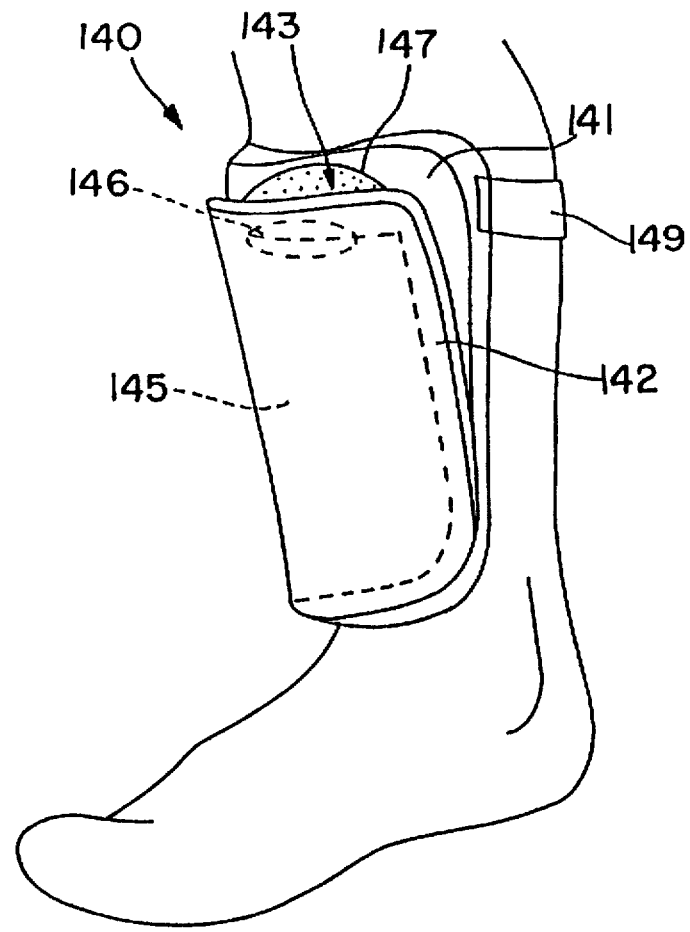
FIG. 21 is a perspective view of an embodiment of the invention which acts as a replaceable protective padding insert in a pad cover.
Figure 22:
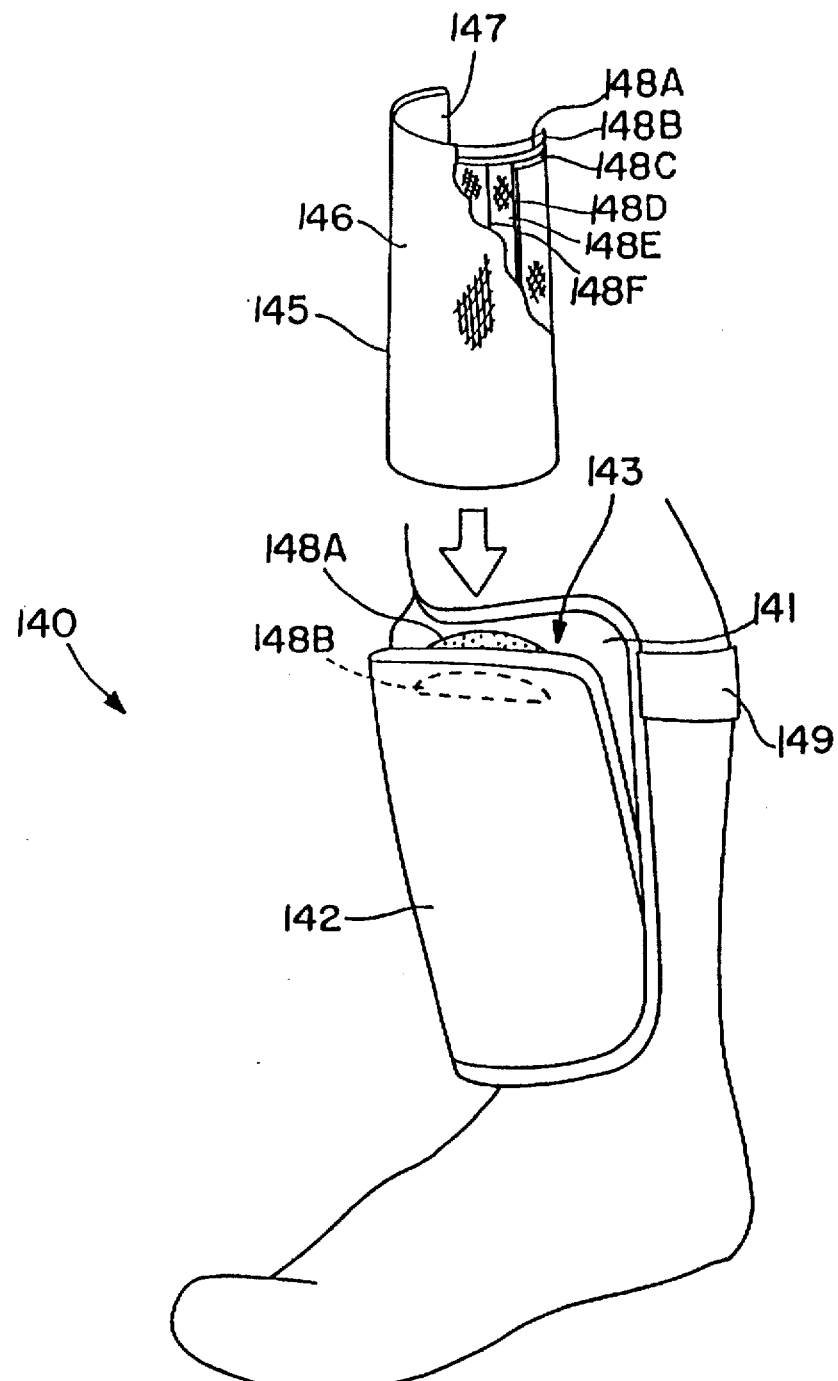
FIG. 22 is a perspective view, with parts broken away, of an embodiment of the invention as shown in FIG. 11.

Referring now to FIGS. 21 and 22, a shin guard 140 is shown. Front and back fabric layers 141 and 142 are connected together on the bottom and sides by, for example, sewing, to form a double layer fabric structure defining a pocket. The pocket is accessed by a top access opening 143 to permit insertion of and removal from the pad cover of a protective pad 145 according to the invention. The pad 145 includes inner and outer cover layers 146 and 147 enveloping an intermediate layer 148 formed of a plurality of layers of fiberglass fiber 148A–F impregnated with a moisture-reactive resin system as described above. The protective pad 145 may be molded to the leg separately as described above and then used in connection with the shin guard 140 or first placed in the pocket of the shin guard 140 while still flexible and molded to the leg while in the shin guard 140. Since the moisture-reactive system affects only the pad 145, the flexibility of the shin guard 140 is not affected.

As is shown in FIG. 22, the protective pad 145 is inserted into the pocket formed by the front and back fabric layers 141 and 142. Complementary male and female hook and loop fastener members 148A and 148B sewn onto the front and back fabric layers 141 and 142 permit the pocket to be closed with the pad 145 contained in it.

A strap 149 may be used to retain the shin guard 140 snugly on the leg.

Figure 23:
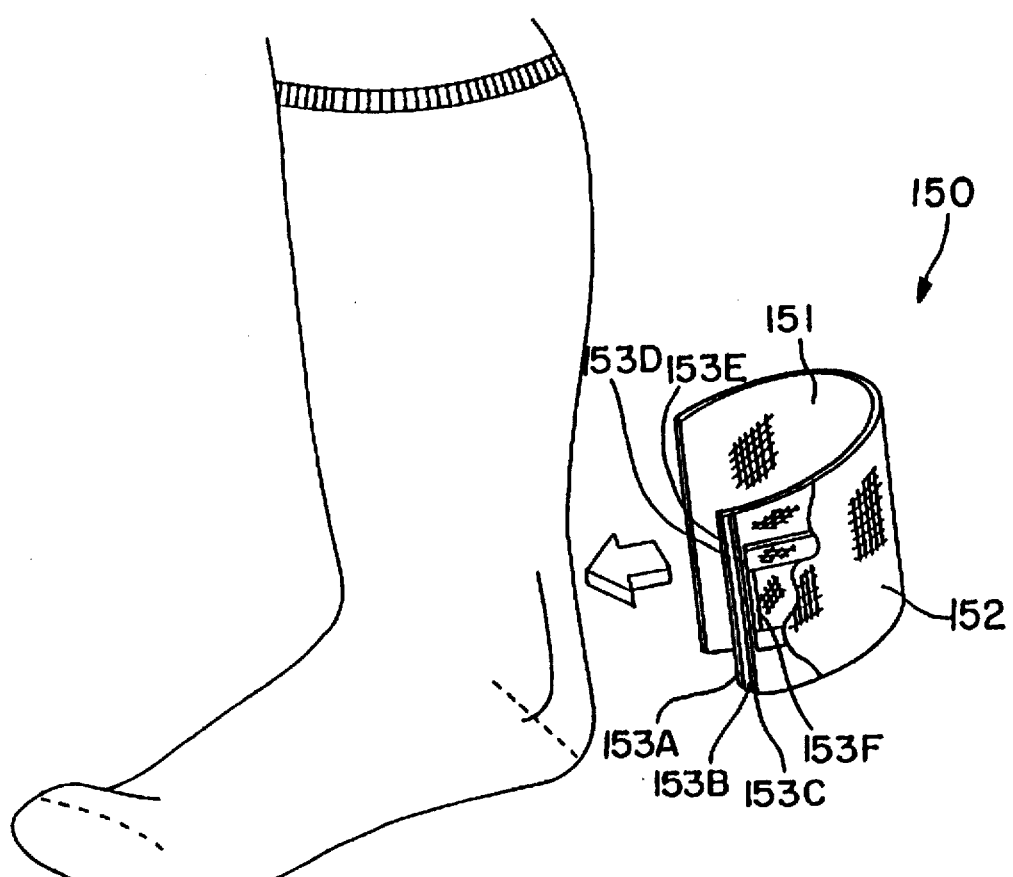
FIG. 23 is a perspective view, with parts broken away, of an achilles heel protector according to the invention.

Referring now to FIG. 23, an achilles tendon protector 150 is shown, and is intended to be molded to the back of the foot in the area of the achilles tendon. Protector 150 includes an inner cushion layer 151, and outer layer 152, and an intermediate layer 153. The intermediate layer is comprised of individual fiberglass layers 153A–F in the "pyramid" form described above.

The fiberglass fabric of the layers 153A–F is impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure.

Protector 150 is applied to the achilles tendon area of the foot while flexible, as described above with reference to FIGS. 11–15. Once hardened, it can be placed back on the foot over an under sock and under a game sock to protect the back of the foot, and particularly the achilles tendon from impact damage. Note that whereas the above-described pads are placed on the leg with the length of the pad extending axially along the length of the leg, the achilles tendon protector 150 is placed on the foot so as to extend radially around the rear portion of the foot. The same pyramid structure described above is used in the achilles tendon protector 150, and as with the above-described pads, the layers of fiberglass extend in the lengthwise direction. Therefore, according to FIG. 23, the top and bottom of the achilles tendon protector is relatively more flexible than the central area extending around the protector from one side of the foot to the other.

The particular embodiments disclosed above are for purposes of illustration. Many other variations are possible while remaining within the scope of the invention. Several other possible constructions for the intermediate layer according to the invention are shown in FIGS. 24A–27B. In each case, the "A" illustration shows the arrangement of the multiple layers of fiberglass fabric, and the "B" illustration shows the same construction in its position as formed around a body part such as a leg.

Figure 24A:
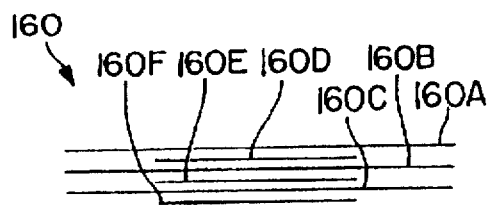
FIGS. 24A, 24B; 25A, 25B; 26A, 26B; and 27A, 27B are simplified vertical cross-sections of the intermediate layer of the protective padding of the invention according to several variations, shown in their respective unmolded and molded conditions.
Figure 24B:
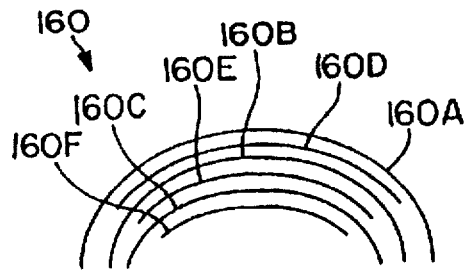

FIGS. 24A and B show an intermediate layer 160 in its original and formed configurations. Intermediate layer 160 includes separate, relatively wide fiberglass layers 160A, B and C, alternated with relatively narrow fiberglass layers 160D, E and F. These layers 160A–F are impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure.

Figure 25A:
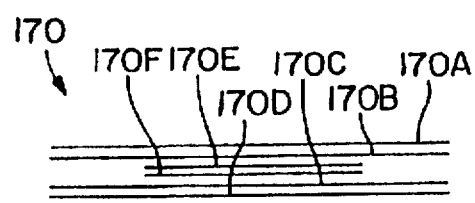
Figure 25B:
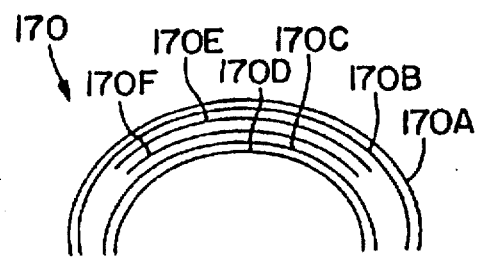

FIGS. 25A and B show an intermediate layer 170 in its original and formed configurations. Intermediate layer 170 includes separate, relatively wide fiberglass layers 170A, B, C and D, with two narrow fiberglass layers 170E and F positioned in the middle of the layer 170 between fiberglass layers 170B and C. The fiberglass layers 170A–F are impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure.

Figure 26A:
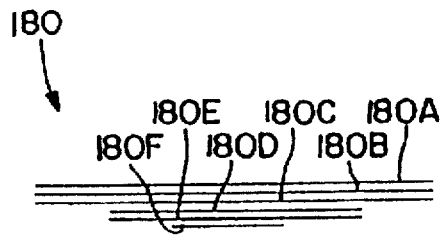
Figure 26B:
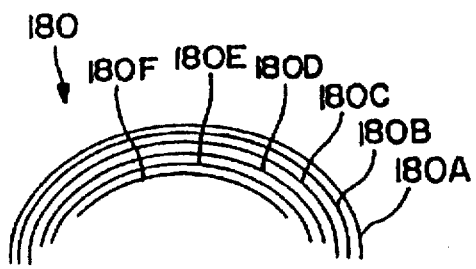

FIGS. 26A and B show an intermediate layer 180 in its original and formed configurations. Intermediate layer 180, very similar to the one shown in FIGS. 16 and 17, but is included to illustrate that the relative dimensions of the various layers can vary with respect to each other, even though the overall configuration of the intermediate layer stays the same. In FIGS. 26A and 26B the narrower layers decrease in width to a greater degree than in the example shown in FIG. 16 and 17. Whereas in FIGS. 16 and 17 the layers are five, four and three inches wide, respectively, in FIGS. 26A and 26B, the layers 180A, B and C are five inches, whereas the layers 80D and E are three inches, and the innermost layer 80F is two inches wide. The layers 80A–F are impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure.

Figure 27A:
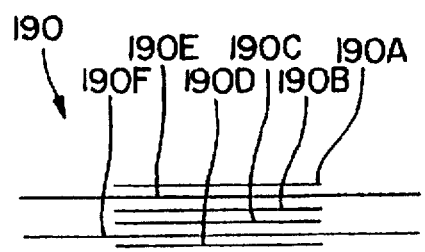
Figure 27B:
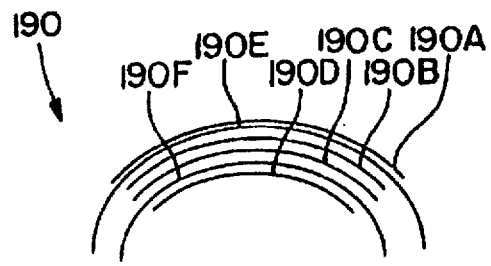

FIGS. 27A and B show an intermediate layer 190 in its original and formed configurations. Intermediate layer 190 includes separate, relatively narrow fiberglass layers 190A, B, C and D, with two relatively wide fiberglass layers 190E and F positioned in the middle of the layer 190 between fiberglass layers 190A and 190B, and 190C and 190D, respectively. The fiberglass layers 190A–F are impregnated or coated with a moisture-curable resin such as polyisocyanate as described in full in the present applicant's U.S. Pat. No. 4,770,299 and above. The reactive system remains stable when maintained in substantially moisture-free conditions but hardens upon exposure to sufficient moisture to form a rigid, self-supporting structure.

The number of layers of fiberglass in the intermediate layer can be varied to take into account anticipated use conditions. Also, as mentioned above, other materials such as polypropylene can be used in substitution for some of the layers. Also, even though the stitches by which the layers are held together are not shown in FIGS. 24A–27B, it is understood that the layers will be stitched together with wide, loose stitches to keep the layers together as a unit while permitting shifting as needed permit the layers to conform to the curvature of the body part to which the pad is being molded.

A protective pad according to several varying embodiment for being molded onto a body part to be protected is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A medical bandaging product, comprising:
    (a) a storage package formed of moisture-impervious material and sealable to prevent entry of moisture;
    (b) a medical material positioned in said storage package and sealed therein against entry of moisture until use, said medical material comprising:
        (i) a substrate having a variable thickness with a relatively thick predetermined central area to provide rigidity, and relatively thin predetermined edge areas to provide less rigidity to the edge areas for ease in molding the medical material around a part of a patient to be bandaged;
        (ii) a reactive system impregnated into or coated onto all areas of said substrate, said system remaining stable when maintained in substantially moisture-free conditions and hardening upon exposure to sufficient moisture to form a rigid, self supporting structure; and
        (iii) a protective wrapping enclosing said substrate along its length to provide a barrier between the substrate and the skin of the patient when the material is in use.

2. A medical bandaging product according to claim 1, wherein said substrate comprises a plurality of overlaid layers of fabric, some of said overlaid layers of fabric having a width greater than others of said layers to collectively define the variable thickness substrate.

3. A medical bandaging product according to claim 2, wherein said fabric layers comprise fiberglass.

4. A medical bandaging product according to claim 3, wherein at least some of said fabric layers comprise woven fiberglass and at least some of said plurality of fiberglass fabric layers comprise nonwoven fiberglass.

5. A medical bandaging product according to claim 4, wherein said plurality of layers of fiberglass comprises at least five layers.

6. A medical bandaging product according to claim 2, wherein said overlaid layers fabric are sewn together with stitches in order to provide stability to the protective pad as the medical material is formed around the body part to be protected.

7. A medical bandaging product according to claim 6, wherein said stitches are sufficiently loosely placed in the substrate to permit substantial shifting of the individual layers relative to each other as the medical material is formed around the body part to be protected.

8. A medical bandaging product according to claim 2, wherein said medical material is pre-cut to a length suitable for a single use and said storage package is sized to receive said single use medical material.

9. A medical bandaging product according to claim 2, wherein said medical bandaging product is in roll form for being dispensed in user-determined lengths suitable for a given medical use, and said storage package comprises an elongate sleeve formed of moisture-impervious material and sealable to prevent entry of moisture, and wherein said medical material comprises an elongate substrate having substantially the same length as the sleeve positioned in said sleeve and sealed therein against entry of moisture until use.

10. A medical bandaging product according to claim 9, and including means for resealing said sleeve against entry of moisture after a user-determined length of said bandaging product has been dispensed for use to prevent hardening of said substrate remaining in said sleeve.

11. A medical bandaging product according to claim 2, wherein at least some of said fabric layers comprise woven fiberglass.

12. A medical bandaging product according to claims 1, 2, 8 or 9, wherein said protective wrapping comprises a soft, flexible material covering at least one side of said substrate along its length to provide a cushioning barrier between the substrate and the skin of a patient when the material is in use.

13. A medical bandaging product according to claim 12, wherein said protective wrapping encircles the substrate along its length.

14. A medical material, comprising:
  (a) a substrate having a variable thickness with a relatively thick predetermined central area to provide rigidity, and relatively thin predetermined edge areas to provide less rigidity to the edge areas for ease in molding the medical material around a part of a patient to be bandaged;
  (b) a reactive system impregnated into all areas of or coated onto said substrate, said system remaining stable when maintained in substantially moisture-free conditions and hardening upon exposure to sufficient moisture to form a rigid, self supporting structure; and
  (c) a protective wrapping enclosing said substrate along its length to provide a barrier between the substrate and the skin of a patient when the material is in use.

15. A medical material according to claim 14, wherein said substrate comprises a plurality of overlaid layers of fabric, some of said overlaid layers of fabric having a width greater than others of said layers to collectively define the variable thickness substrate.

16. A medical material according to claim 15, wherein said fabric layers comprise fiberglass.

17. A medical material according to claim 15, wherein at least some of said fabric layers comprise woven fiberglass.

18. A medical material according to claim 15, wherein at least some of said plurality of fiberglass fabric layers comprise woven fiberglass and at least some of said plurality of fiberglass fabric layers comprise nonwoven fiberglass.

19. A medical material according to claim 18, wherein said plurality of layers of fiberglass comprises at least five layers.

20. A medical material according to claim 15, wherein said overlaid fiberglass layers are sewn together with stitches in order to provide stability to the protective pad as the medical material is formed around the body part to be protected.

21. A medical material according to claim 20, wherein said stitches are sufficiently loosely placed in the substrate to permit substantial shifting of the individual layers relative to each other as the medical material is formed around the body part to be protected.

22. A medical material according to claim 15, wherein said medical material is pre-cut to a length suitable for a single use and said storage package is sized to receive said single use medical material.

23. A medical bandaging product according to claim 15, wherein said medical bandaging product is in roll form for being dispensed in user-determined lengths suitable for a given medical use, and said storage package comprises an elongate sleeve formed of moisture-impervious material and sealable to prevent entry of moisture, and wherein said medical material comprises an elongate substrate having substantially the same length as the sleeve positioned in said sleeve and sealed therein against entry of moisture until use.

24. A medical bandaging product according to claims 14, 15, 22 or 23, wherein said protective wrapping comprises a soft, flexible material covering at least one side of said substrate along its length to provide a cushioning barrier between the substrate and the skin of a patient when the material is in use.

25. A medical bandaging product according to claim 24, wherein said protective wrapping encircles the substrate along its length.

26. A medical material, comprising:
  (a) a substrate having a variable thickness with a relatively thick predetermined central area to provide rigidity, and relatively thin predetermined edge areas to provide less rigidity to the edge areas for ease in molding the medical material around the part of the patient to be bandaged;
  (b) a reactive system impregnated into or coated onto both the central area and the edge areas of said substrate, said system remaining stable when maintained in substantially moisture-free conditions and hardening upon exposure to sufficient moisture to form a rigid, self-supporting structure; and
  (c) a protective wrapping enclosing said substrate along its length to provide a barrier between the substrate and the skin of a patient when the material is in use.

27. A medical material, comprising:
  (a) a substrate having a variable thickness with a relatively thick predetermined central area to provide rigidity, and relatively thin predetermined edge areas to provide less rigidity to the edge areas for ease in molding the medical material around the part of the patient to be bandaged;
  (b) a reactive system impregnated into or coated onto all of the central area and at least some of the edge areas of said substrate, said system remaining stable when maintained in substantially moisture-free conditions and hardening upon exposure to sufficient moisture to form a rigid, self-supporting structure; and
  (c) a protective wrapping enclosing said substrate along its length to provide a barrier between the substrate and the skin of a patient when the material is in use.

\* \* \* \* \*

UNITED STATES PATENT AND TRADEMARK OFFICE
CERTIFICATE OF CORRECTION

PATENT NO. : 5,755,678
DATED : May 26, 1998
INVENTOR(S) : Parker et al.

Page 1 of 1

It is certified that error appears in the above-identified patent and that said Letters Patent is hereby corrected as shown below:

Drawings,
Delete Figure 4, and substitute therefor the Figure consisting of Fig. 4, as shown below.

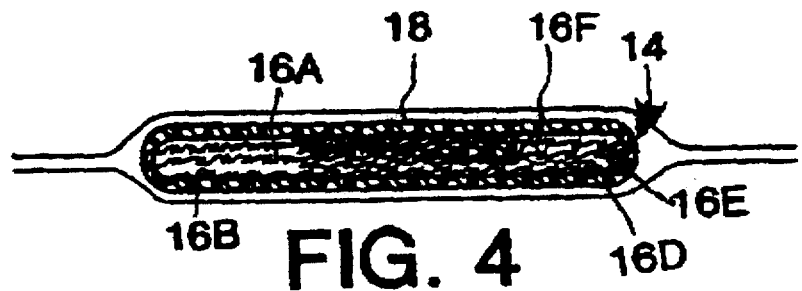

Signed and Sealed this

Twenty-third Day of April, 2002

Attest:

JAMES E. ROGAN
Director of the United States Patent and Trademark Office

Attesting Officer